United States Patent [19]

McDonald et al.

[11] Patent Number: 5,055,292
[45] Date of Patent: Oct. 8, 1991

[54] VACCINES FOR COCCIDIOSIS COMPRISING LIVE SPORULATED OOCYSTS FROM STRAINS OF EIMERIA SPECIES

[75] Inventors: Vincent McDonald, Cambridge; Martin W. Shirley, Buckden, both of United Kingdom

[73] Assignee: National Research Development Corporation, London, United Kingdom

[21] Appl. No.: 506,538

[22] Filed: Apr. 9, 1990

Related U.S. Application Data

[63] Continuation of Ser. No. 85,869, Aug. 17, 1987, abandoned.

[30] Foreign Application Priority Data

Aug. 18, 1986 [GB] United Kingdom ................ 8620059
Dec. 10, 1986 [GB] United Kingdom ................ 8629475

[51] Int. Cl.$^5$ .......................................... A61K 39/012
[52] U.S. Cl. ...................................... 424/88; 424/93; 435/243; 435/245; 435/258; 435/947
[58] Field of Search .................... 424/88, 93; 435/243, 435/245, 258, 947

[56] References Cited

U.S. PATENT DOCUMENTS

| 4,438,097 | 3/1984 | Shirley | 424/88 |
|---|---|---|---|
| 4,639,372 | 1/1987 | Murray et al. | 530/403 |
| 4,724,145 | 2/1988 | Murray | 530/350 |
| 4,808,404 | 2/1989 | Bhogal | 424/93 |
| 4,863,731 | 9/1989 | Davis | 424/93 |

FOREIGN PATENT DOCUMENTS 2008404B 6/1979 United Kingdom .
2144331A 3/1985 United Kingdom .

OTHER PUBLICATIONS

Giambrone, Poultry Science, 1980, pp. 1715-1721, vol. 59(8).
Danforth et al., Poultry Science, 1983, 62, pp. 2145-2151.
Lakielic et al., Bi Vet J. 7/1986, 132(4), pp. 416-422 (Abst. only).
P. L. Long et al., Avian Pathology, 6: 77-92; "Elmeria: Immunisation of Young Chickens Kept in Litter Pens".
M. E. Rose & P. L. Long in "Vaccines Against Parasites", Sumposia of the British Society for Parasitology, vol. 18, ed. A.E.R. Taylor & R. Muller, pub. Blackwell Scientific Publications Oxford 1980, pp. 57-74.
M. W. Shirley, J. Parasitol. 66, 172-173 (1980).
P. L. Long & M. E. Rose, World's Poultry Science Journal 38, 85-96 (1982).
P. L. Long, B. J. Millard, A. F. Batty & C. Davidson, Avian Pathology 11, 131-144 (1982).
Report of the Houghton Poultry Research Station 1981-1982, published by Houghton Poultry Research Station, Houghton, Huntingdon, Cambs. (1983), pp. 64 and 65.
Report of the Houghton Poultry Research Station 1983-1984, published by Houghton Poultry Research Station, Houghton, Huntingdon, Cambs. (1985), pp. 66-68.
M. E. Rose, Proc. Intl. Symp. Royal Agricultural Soc. England, 26 Jun. to 2 Jul. 1985, pub. Royal Agricultural Society, pp. 163-173.
Houghton Poultry Research Station, brochure (1986), first page of "Parasitology".
Report of The Agricultrual and Food Research Council for the year 1984/85, pub. AFRC, London 1985, pp. 57-59.
Animal Pharm. No. 93 (29th Nov. 1985), p. 6.
T. K. Jeffers, Research in Avian Coccidiosis, Proceedings of the Georgia Coccidiosis Conference (No. 19-21, 1985), ed. L. R. McDougald, L. P. Joyner & P. L. Long, pub. University of Georgia, Dept. of Poultry Science, Athens, Ga. U.S.A., Jul. 1986, pp. 482-501.
V. McDonald & M. W. Shirley, ibid., pp. 502-509.
L. R. McDougald, Zootecnica International, 20 and 22 (May 1986).
M. W. Shirley & B. J. Millard, Avian Pathology 15, 629-638 (1986).
C. A. Sutton, M. W. Shirley and V. McDonald, J. Parasitol 72 (6), 965-967 (1986).
M. W. Shirley, Abstracts of the British Society for Parasitology Silver Jubilee Spring Meeting, Edinburgh University, 25-27 Mar. 1987, p. 58.
Report of the Houghton Poultry Research Station 1985-1986, pub. by Houghton Poultry Research Station (now the Institute for Research on Animal Diseases, Houghton Laboratory), Houghton, Huntingdon, Cambs. (May 1987), pp. 73, 76, 77 & 79-85.
V. McDonald, S. Ballingall & M. W. Shirley, Parasitology 84, 21-30 (1982).
V. McDonald & S. Ballingall, Molecular & Biochemical Parasitology (Abstracts presented at the proceeding of the 5th International Congress of Parasitology, Toronto 7-Aug. 1982) edited by M. Müller, W. Gutteridge & P. Köhler, pub. Elsevier Biomedical Press, Amsterdam 1982, p. 211.
V. McDonald & S. Ballingall, Parasitology 86, 361-369 (1983).
J. K. Johnson and P. L. Long, Poultry Science 64, Supplement 1, 123 (1985).
J. K. Johnson, P. L. Long & M. E. McKenzie, Avian Pathology 15, 697-704 (1986).
M. W. Shirley, V. McDonald & M. A. Bellatti, Avian Pathology 15, 705-717 (1986).

(List continued on next page.)

Primary Examiner—Garnette D. Draper
Attorney, Agent, or Firm—Bacon & Thomas

[57] ABSTRACT

Vaccines active against coccidiosis in domestic fowls contain attenuated precocious strains of Eimeria species.

18 Claims, No Drawings

OTHER PUBLICATIONS

V. McDonald, M. W. Shirley & M. A. Bellatti, Experimental Parasitology 61, 192–200 (1986).
V. McDonald & S. Ballingall, Parasitology 86, 371–379 (1983).
V. McDonald & M. W. Shirley, Parasitology 88, 37–44 (1984).
V. McDonald, M. W. Shirley & H. D. Chapman, Res. Vet. Sci. 39, 328–332 (1985).
M. W. Shirley, M. A. Bellatti & B. J. Millard, Parasitology 82, 215–226 (1982).
M. W. Shirley, Parasitology 84, i (1982).
V. McDonald & S. Ballingall, Parasitology 84, i (1982).
M. W. Shirley, Parasitology 87, viii (1983).
M. W. Shirley & M. A. Bellatti, Avian Pathology 13, 657–668 (1984).
M. W. Shirley, V. McDonald, H. D. Chapman & B. J. Millard, Avian Pathology 13, 669–682 (1984).
T. K. Jeffers, J. Parasitol. 61, 1083–1090 (1975).
L. R. McDougald & T. K. Jeffers, Science (U.S.A.) 192, 258 and 259 (1976).
L. R. McDougald & T. K. Jeffers, J. Protozoology 23, 530–534 (1976).
T. K. Jeffers, Z. Parasitenkunde 50, 251–256 (1976).
J. Johnson, M. Reid & J. K. Jeffers, Poultry Science 58, 37–41 (1979).
J. Kucera & P. Bedrnik, J. Protozoology 30, 29A (1983).
P. Bedrnik, J. Kucera, P. Jurkovic & A. Firmanova, Research in Avian Coccidiosis, Proceedings of the Georgia Coccidiosis Conference (Nov. 19–21, 1985) ed. L. R. McDougald, L. P. Joyner and P. L. Long, pub. University of Georgia, Dept. of Poultry Science, Athens, Ga. U.S.A., Jul. 1986, pp. 510–525.
V. McDonald, M. E. Rose & T. K. Jeffers, Parasitology, 93, 1–7 (1986).
V. McDonald, M. W. Shirley & B. J. Millard, Avian Pathology 15, 323–336 (1986).

VACCINES FOR COCCIDIOSIS COMPRISING LIVE SPORULATED OOCYSTS FROM STRAINS OF EIMERIA SPECIES

This application is a continuation of application Ser. No. 07/085,869, filed Aug. 17, 1987, now abandoned.

This invention concerns vaccines active against coccidiosis in domestic fowls and attenuated lines of Eimeria for use in such vaccines.

Coccidiosis of domestic fowls, especially the domestic chicken *Gallus domesticus* (referred to hereinafter simply as chickens), is an economically important disease caused by any of seven species of Eimeria which by developing and multiplying within the epithelial cells of the intestine cause lesions therein. Most poultry producers use prophylactic drugs to prevent outbreaks of the disease, typical signs of which are anorexia, loss of weight, diarrhoea and blood in the faeces. Despite the use of such drugs, however, coccidiosis remains a major problem and its annual cost to the poultry industry has been estimated at $500 million, of which half is attributed to the cost of medication.

However, the life of many anticoccidial drugs has proved to be relatively short due to the emergence of resistant strains or to lack of activity against all the strains or species of Eimeria. In birds other than broilers, medication is permitted with only one drug (amprolium) during egg production. Furthermore, such treatments during the rearing period often interfere with acquisition of immunity, thus rendering the birds susceptible when the drugs are withdrawn.

It has also been proposed to control coccidiosis immunologically using a live vaccine consisting of a suspension of fully virulent oocysts of Eimeria species. However, the technique relies on self-reinfection with oocysts resulting from the original dosing and is only suitable for birds kept on litter, which has to be managed in such a way as to provide favourable conditions for the survival and sporulation of the oocysts. Another problem is to ensure that each bird receives the correct initial dose; too large an inoculum of some species will cause pathogenic effects while too small an inoculum will result in insufficient immunisation to counter the challenge from virulent oocysts in the litter. These difficulties probably account for most of the failures experienced when such a vaccine has been used for broilers.

The life cycle of all the Eimeria species is essentially the same, although each has a preferred site in the intestine for development. Infection takes place by ingestion of sporulated oocysts which in the intestine release sporocysts which in turn release sporozoites. The latter locate themselves in the epithelium and transform into trophozoites. These undergo the process of merogony and become first generation schizonts. Merozoites, are then released and again locate themselves in the epithelium in the intestine and grow to form second generation schizonts. A third or even a fourth generation of schizonts can form in the same way. These schizonts, or the sexual stages developed therefrom are relatively large and are responsible for the tissue damage which is the principal pathogenic effect of the infection.

Subsequently, the merozoites form macrogametocytes and microgametocytes which release microgametes. The former become fertilised by microgametes to form unsporulated oocysts which are released into the intestine and excreted with the faeces. Sporulation takes place in the litter and the inevitable ingestion of this material by the birds leads to further infection with the sporulated oocysts.

The emergence of oocysts in the faeces is known as patency. The time from ingestion of sporulated oocysts to emergence of oocysts in the faeces is termed the prepatent time. This differs between the various Eimeria species.

It has been found that some attenuation of the pathogenicity of the parasites can be achieved by repeated passage in chickens with selection for early appearance of oocysts. In this way populations can be selected with greatly reduced prepatent times and greatly reduced pathogenicity. While the mechanism of such attenuation is not completely understood, it is thought generally to be due to the depletion and/or a reduction in the size of at least one schizont generation, thus reducing tissue damage. Such attenuated lines having shortened prepatent times are commonly termed "precocious lines".

We have found that such attenuation can be achieved while retaining immunogenicity and this provides the possibility of immunological control of coccidiosis using vaccines based on live attenuated, precocious lines of Eimeria. This avoids some of the problems associated with unattenuated live vaccines, in that, in general, exceeding the recommended dose is less likely to lead to pathogenic effects and the accumulation of non-virulent oocysts in the litter will not produce a pathogenic infection in underdosed birds which have not yet developed immunity.

The precocious lines may be obtained from the virulent parent strains, as indicated above, by serial passage in chickens, with collection of oocysts from either the faeces or homogenised caecal tissue, in each case in the first few hours after patency. In this way the prepatent time is progressively reduced. This type of passage is termed a selection passage. In order to increase the numbers of oocysts available, it may be advantageous to collect oocysts at a time between the onset of patency and approximately the prepatent time of the parent strain (neutral passage) or to collect virtually all of the oocysts, including those later than the prepatent time of the parent strain (relaxed passage).

In consideration of the prevalence and pathogenicity of the various Eimeria species, we have concluded that a successful attenuated anticoccidial vaccine should contain at least live attenuated, precocious lines of *Eimeria acervulina*, *Eimeria maxima* and *Eimeria tenella*. It is, in fact, advantageous for live attenuated, precocious lines of *Eimeria necatrix*, *Eimeria mitis* and *Eimeria brunetti* to be present; desirably an attenuated, precocious line of *Eimeria praecox* is also present.

It has been found that certain Eimeria species, notably *Eimeria maxima*, show marked mutual antigenic diversity such that infection with some strains will protect chickens only to a limited extent against challenge with certain other strains of the same species. Consequently, it may be desirable to include in an anticoccidial vaccine two or possibly more lines derived from mutually immunologically diverse strains of Eimeria, notably *Eimeria maxima*.

In formulating a vaccine containing a number of attenuated lines of Eimeria species, it is important that these are present in proportions suitable to produce a satisfactory level of immunity against the relevant Eimeria species without significant pathogenic effects. The appropriate proportions are thus based inter alia on the immunogenicity and pathogenicity of the attenuated lines. We have determined these parameters in respect of attenuated, precocious lines of all the relevant Eimeria species. Although some information on such parameters has been published in respect of the separate Eimeria species, this has not been in a form which would permit calculation of the most appropriate proportions of the respective attenuated lines for inclusion in an anticoccidial vaccine.

In general, the preferred ratios of the numbers of sporulated oocysts of each of the separate attenuated, precocious lines in the vaccine (where present) can conveniently be expressed in terms of the number of sporulated oocysts relative to 100 sporulated oocysts of E. acervulina: namely as follows:

E. maxima 15-30, preferably 15-25, more preferably 18-22 e.g. about 20.

E. tenella 70-110, preferably 75-105, more preferably 95-105, e.g. about 90.

E. brunetti 15-30, preferably 15-25, more preferably 18-22, e.g. about 20.

E. mitis 180-220, preferably 190-210, more preferably about 200.

E. necatrix 70-110, preferably 90-110, more preferably 75-105, e.g. about 90.

E. praecox 15-25, preferably 18-22, more preferably about 20.

As indicated above, it may be desirable to include two or more immunologically diverse attenuated lines of an Eimeria species, for example E. maxima, and the above numerical values apply to each of the separate lines when present.

According to one feature of the invention, therefore, we provide an attenuated anticoccidial vaccine containing live attenuated, precocious lines of at least E. acervulina, E. maxima and E. tenella, the number of sporulated oocysts of each separate Eimeria line present per 100 sporulated oocysts of E. acervulina being for E. maxima 15-30 and E. tenella 70-110.

Where sporulated oocysts of other live attenuated, precocious Eimeria lines are present, the numbers relative to E. acervulina may be in accordance with the numerical values stated above.

Attenuation can conveniently be expressed in terms of the prepatent time in a standard breed of chicken; for the purposes of this specification, the prepatent time is defined as the time between oral ingestion of washed sporulated oocysts by Light Sussex chickens (maintained coccidiosis-free prior to inoculation and transferred to wire-floored cages for experimentation) and the first emergence of oocysts in the faeces.

In general, in order to achieve a useful degree of attenuation, the prepatent time of attenuated lines should be shorter than that of the non-attenuated parent strain. However, selection for excessively short prepatent times leads to reduction in reproduction to the extent that insufficient parasites are present in the intestine to produce the required immunological response. Consequently, it is important that prepatent times of the selected lines should be within relatively narrow limits.

Advantageous ranges of prepatent times of the separate attenuated, precocious lines of Eimeria species for use in the vaccine are as listed below. The reduction in prepatent time as compared with the parent strain is given in parenthesis with reference to the shortest prepatent time.

| | |
|---|---|
| E. acervulina | 60-84 hours (reduction of up to 37 hours from the 97 hour prepatent time of the parent strain), preferably 64-78 hours, more preferably 66-72 hours. |
| E. maxima MFP | 80-118 hours (reduction of up to 31 hours from the 121 hour prepatent time of the parent strain), preferably 104-110 hours, more preferably 108-110 hours. |
| E. maxima CP | 90-120 hours (reduction of up to 36 hours from the 126 hour prepatent time of the parent strain), preferably 100-118 hours, more preferably 110-120 hours. |
| E. tenella | 90-125 hours, (reduction of up to 42 hours from the 132 hour prepatent time of the parent strain), preferably 107-120 hours. |
| E. necatrix | 90-126 hours (reduction of up to 48 hours from the 138 hour prepatent time of the parent strain), preferably 100-120 hours. |
| E. mitis | 60-84 hours (reduction of up to 41 hours from the 101 hour prepatent time of the parent strain), preferably '64-78 hours, more preferably 64-72 hours. |
| E. brunetti | 70-100 hours (reduction of up to 50 hours from the 120 hour prepatent time of the parent strain), preferably 70-90 hours, more preferably 75-88 hours. |
| E. praecox | 44-75 hours (reduction of up to 40 hours from the 84 hour prepatent time of the parent strain), preferably 64-75 hours, more preferably 64-70 hours. |

According to a second feature of the invention we provide an attenuated anticoccidial vaccine containing at least an attenuated, precocious line of E. acervulina, having a prepatent time in the range 60-84 hours, of E. maxima having a prepatent time in the range 80-120 hours and of E. tenella having a prepatent time in the range 90-125 hours.

When other attenuated, precocious Eimeria lines are present, their prepatent times are desirably in accordance with the prepatent times listed above.

In general, it is desirable that the attenuated lines, selected by their prepatent times above, should be stable on passaging in chickens in order to avoid reversion to virulence when, as is normally inevitable, sporulated oocysts appearing in the faeces after vaccination are ingested and thus passaged a number of times before the birds become satisfactorily immunised. Reversion to virulence could thus lead to a pathogenic infection. If the birds are prevented from ingesting faeces, for example if kept in wire-floored cages, this problem may not occur and stability of attenuation may not be essential. Furthermore, some species are sufficiently immunogenic that the birds are immunised by the time the oocysts have been passaged once or twice. However, in general, the optimal selected attenuated strains are those found to be stable on relaxed passaging at least 5 times, and desirably at least 7 times, in the host chickens.

A number of attenuated, precocious Eimeria lines suitable for use in the present invention have been deposited in the form of sporocysts at the European Collection of Animal Cell Cultures, PHLS Center for Applied Microbiology & Research, Porton Down, Salisbury, Wiltshire, SP4 0JG, England as patent deposits under the Budapest Treaty on the International Recognition of the Deposit of Microorganisms for the Purposes of Patent Procedure, under the following numbers and dates:

| | Line | Code* | Number | Date of Deposit |
|---|---|---|---|---|
| 1. | E. acervulina | HP71s + 13 | ECACC 86072203 | 22 July 1986 |
| 2. | E. brunetti | HP27s + 8 | ECACC 86072204 | 22 July 1986 |
| 2A. | E. brunetti | HP27.2s + 7 | ECACC 86112013 | 20 November 1986 |
| 3. | E. maxima | MFP15s + 11 | ECACC 86112011 | 20 November 1986 |
| 3A. | E. maxima | CP12s + 11 | ECACC 86112012 | 20 November 1986 |
| 4. | E. mitis | HP12s + 11 | ECACC 86072206 | 22 July 1986 |
| 5. | E. necatrix | HP42.2s + 8 | ECACC 86072202 | 22 July 1986 |
| 6. | E. praecox | HP21.2s + 2 | ECACC 86072205 | 22 July 1986 |
| 7. | E. tenella | HP38s + 10 | ECACC 86072201 | 22 July 1986 |

The attenuated lines are identified according to the following code: the parent strain is given a code-letter indicating its origin, e.g. *E. acervulina* H or *E. maxima* C. The attenuated or precocious lines are coded with the additional letter P followed by a number indicating the number of serial passages to which they have been subjected. Where a sub-line was established from a single oocyst of the line the letter s is added and where the sub-line has been subjected to serial neutral or relaxed passage, a further number is added corresponding to the number of such passages. Thus *E. acervulina* HP 71s+13 refers to a precocious line derived by 71 passages of the H strain of *E. acervulina* with selection for early development of oocysts, followed by passage from a single oocyst and then thirteen serial relaxed or neutral passages. Where passage from a single oocyst or sporozoite is repeated, "2s" is indicated, followed by the number of relaxed or neutral passages after the second "s" passage.

In another aspect the invention provides each of the above lines, together with precocious attenuated immunogenic mutants and variants thereof. For example these may have prepatent times in the ranges listed above whereby they may be distinguished from their parent, unattenuated, strains. Such variant lines include progeny resulting from further passaging and other variants indistinguishable from the deposited lines. Mutants include those resulting from natural or other mutation. The lines according to the invention include all the forms in the life cycle of the organisms and thus include sporulated and unsporulated oocysts, sporocysts, sporozoites, trophozoites, schizonts, merozoites, microgametocytes, microgametes and macrogametocytes.

It has been found useful, in order to stabilise the traits of a precocious line to establish a subline line by passaging a single oocyst of the precocious line or if desired a single sporocyst or sporozoite thereof. The invention includes particularly such sub-lines of precocious lines collateral to the above lines (having been derived from the same parent) or descendents therefrom (having been derived from the deposited lines by further passaging, especially neutral or relaxed passaging as previously described).

The invention includes each of the above lines and variants individually and their use in vaccinating chickens against a coccidial infection. They can be used individually, in any combination of two or more or in any combination of one or more lines of the invention with one or more other live attenuated Eimeria organisms, in any proportions but most preferably those recited hereinbefore. The invention further includes chicken feed or drink, including water, containing parasites of the live attenuated lines.

The oocysts of the above deposited lines and their mutants and variants are morphologically indistinguishable from those of the parent strains. The precocious lines differ from the parent strains in their prepatent times, endogenous development, pathogenicity and reproductive potential. The characteristics of the various Eimeria species are fully set out by Long P. L. and Reid W. M. (1982: A Guide for the Diagnosis of Coccidiosis in Chickens; University of Georgia Research Report 404) and Joyner L. P. (1978: Identification and Diagnosis, Avian Coccidiosis, Poultry Science Symposium No. 13, British Poultry Science Ltd). One method of identifying the various species is enzyme electrophoresis, to detect, for example, variants of the enzymes glucose phosphate isomerase and lactate dehydrogenase. The characteristic variants have been categorised by Shirley M. W. (Proceedings of the Georgia Coccidiosis Conference 1985). The attenuated lines are identical with the parent strains in respect of these characteristic enzyme variants.

Mutants of the above deposited lines may be obtained for example by further application of selection pressure as described above or other techniques. (Goodenough and Levine, Genetics, Holt, Rinehart and Winston Inc. 1974)

Characteristics of some of the asexual stages of the deposited lines and mutants and variants thereof, as determined from measurements of stained and fixed sections of infected gut, are as follows:

*E. acervulina*: the majority of the gametocytes develop directly from the third generation of schizonts; the mean sizes of the schizonts and the mean numbers of merozoites therein are substantially similar to those of the parent strain.

*E. brunetti*: the majority of gametocytes develop directly from the first or second generation of schizonts; the mean sizes of the first and second generation of schizonts are slightly lower than those of the parent strain while the number of merozoites per schizont is approximately the same.

*E. maxima* MFP and *E. maxima* CP: gametocytes appear at about 72 hours or earlier post infection; the mean sizes of the schizonts and the mean numbers of merozoites therein are substantially similar to those of the parent strain.

*E. mitis*: gametocytes appear at about 66 hours and develop mainly from third generation merozoites; the mean size of the first generation of schizonts and the mean numbers of merozoites therein are lower than in the case of the parent strain.

*E. necatrix*: the mean size of the second generation of schizonts and the mean numbers of merozoites therein are significantly lower than in the case of the parent strain.

*E. praecox*: the majority of gametocytes develop directly from the third generation of schizonts; the mean sizes of the schizonts and the mean numbers of merozoites therein are substantially similar to those of the parent strain.

*E. tenella*: the majority of gametocytes develop directly from third generation merozoites; the mean size of the second generation of schizonts and the mean numbers of merozoites therein are significantly lower than in the case of the parent strain.

A "dose" of vaccine is the amount provided for one bird. In general, the total number of sporulated oocysts per dose of vaccine may vary between about $2.5 \times 10^2$ and $2 \times 10^5$, more preferably between $5 \times 10^2$ and $6 \times 10^3$. Thus, in general, one dose of vaccine may contain the following numbers of sporulated oocysts of each precocious line of Eimeria present.

| | | |
|---|---|---|
| E. acervulina | 50 to 25,000 | preferably 100 to 2,000 |
| E. maxima | 10 to 5,000 | preferably 20 to 400 |
| E. tenella | 50 to 25,000 | preferably 80 to 2,000 |
| E. brunetti | 10 to 5,000 | preferably 20 to 400 |
| E. mitis | 100 to 50,000 | preferably 200 to 4,000 |
| E. necatrix | 50 to 25,000 | preferably 100 to 2,000 |
| E. praecox | 10 to 5,000 | preferably 20 to 400 |

Where two lines of *E. maxima* are present, e.g. MFP 15s and CP 12s, quantities of each in the range 10 to 5,000, preferably 20 to 400, may be used.

*E. brunetti* ECACC 86112013 is preferred to the collateral line 86072204 on account of improved stability of attenuation following passaging in birds.

In general, the vaccine will comprise a suspension of the oocysts in sterile distilled water containing a suspending agent, for example a polysaccharide suspending agent such as a gum, e.g. xanthan gum or gum acacia, a cellulose derivative, e.g. carboxymethyl cellulose, hydroxypropyl methyl cellulose or microcrystalline cellulose, carageenan, sodium alginate, pectin or starch; a polypeptide suspending agent such as gelatin; a synthetic polymer suspending agent such as polyacrylic acid; or a silicate suspending agent such as magnesium aluminium silicate. In general, the quantity of suspending agent in the vaccine will be in the range 1 to 25 g/liter, preferably 1.5 to 12 g/liter. A preservative may be present to inhibit contamination with other organisms, e.g. formalin at a concentration of, for example, 0.01% w/w.

The concentration of sporulated oocysts in the vaccine may, for example, be in the range $10^7$ to $10^8$/liter.

In general, the vaccine will be administered orally, most conveniently in the feed and/or drinking water of the birds. The vaccine is effective when administered in the drinking water. A single dose may be given to the young chickens, which are advantageously aged between 3 and 10 days, preferably 5 to 10 days. It may also be beneficial, however, to inoculate by the so-called 'trickle' method, that is to provide very low doses of the organisms on successive days to build up immunity. Where the birds are maintained on litter, re-infection by ingestion of excreted oocysts of the precocious organisms may enhance immunisation. The use of the vaccine according to the invention is particularly valuable in treating fowls intended for breeding and the producion of heavy broilers (e.g. fowls reared for 55 days or longer).

Birds receiving vaccine may advantageously be fed one or more antibiotic growth promotors such as avoparcin and virginiamycin. These may advantageously be present in the feed in the concentration range 7.5 to 12.5 ppm, e.g. about 10 ppm.

The pathogenicity of the precocious lines may be determined by examining the body weight changes of infected chickens relative to bodyweight changes for birds with wild-type Eimeria species. When a satisfactory attenuated line has been obtained, it is desirable to establish a sub-line by passage of a single oocyst, sporocyst or sporozoite in order to increase the uniformity of the population and thereby reduce the probability of a reversion to virulence, i.e. instability. It may be desirable to repeat this step. Subsequently, the subline may be subjected to a number of successive relaxed passages to test for stability. When a stable attenuated subline has been obtained it may be subjected to relaxed passage in order to produce relatively large numbers for incorporation in the vaccine.

The collected oocysts will normally be unsporulated and will require sporulation prior to re-inoculation, for example by suspension in an aqueous solution of an oxidant such as 2% aqueous potassium dichromate and incubation, e.g. at 29° C., with forced aeration (the oxygen rich environment encourages sporulation and also inhibits bacterial growth). After sporulation the oocysts may be treated with one or more antibacterial substances to avoid contamination by other microorganisms. The oocysts may be collected from faeces or homogenised caecal tissue by salt flotation (Long, Proceedings of the 9th Symposium of the British Society for Parasitology, pp 65–67, 1971).

The following examples are given by way of illustration only:

EXAMPLE 1

Preparation of Vaccine

Seed Lot System

Master seeds of each attenuated Eimeria line to be used are held in liquid nitrogen refrigeration. From a sample of each master seed a working seed is prepared by oral inoculation into SPF chickens. Oocysts are recovered from the faeces and/or caeca to make working seeds. The working seed is stored at 4° C. and is used to initiate each vaccine production. Working seed has a shelf life of six months after which it is replaced.

When working seed is prepared, oocysts are only harvested up to about the prepatent time of the wild type parent strain for that species i.e. neutral passage.

When the vaccine is prepared, oocysts are harvested throughout the patent period of the infection i.e. relaxed passage.

Rearing of Chickens

Chickens are hatched from eggs obtained from a certified SPF flock. They are reared in isolation on a diet containing robenidine until 4–6 weeks of age. They are then transferred to the vaccine production accommodation, allocated in groups to separate rooms designated for each Eimeria species and robenidine is withdrawn from the diet 2 days before infection.

Inoculation

Each group of birds is inoculated orally with a previously determined dose of working seed. Inoculation is preferably arranged according to a staggered schedule so that only one species of Eimeria is harvested and processed on one working day.

Harvesting

Faeces are collected although the time and duration of collection varies from species to species. A slurry of faeces (and/or caecal contents) is made in water which is then homogenised. The homogenate is washed through a 150 micron sieve and the washings are centrifuged in a continuous flow bowl centrifuge. The centrifuged deposit is resuspended in saturated salt solution and recentrifuged. The supernatant is collected. This is diluted with water and passed a third time through the centrifuge. The deposit is resuspended in a 2% solution of potassium dichromate.

Sporulation

The oocyst suspension in potassium dichromate solution is incubated at 29° C. for 48 hours with forced aeration to sporulate the oocysts. After sporulation the dichromate solution is removed by centrifugation and the oocysts are treated with 10% chlorox (sodium hypochlorite solution) for 10 minutes. Treated oocysts are resuspended in water and formalin is added to a concentration of 0.05%. The suspension is stored at 4° C.

Blending

Oocyst counts of each bulk oocyst solution suspension are made and calculated volumes of each suspension are mixed with a suspending agent to give a multi component vaccine with oocysts of each species present in the desired proportions. The vaccine is filled into final containers and stored at 4° C.

EXAMPLE 2

1 liter of vaccine containing 4000 doses may be formulated as follows:

| | | |
|---|---|---|
| E. acervulina | HP | $2 \times 10^6$ oocysts |
| E. brunetti | HP | $4 \times 10^5$ oocysts |
| E. maxima | MFP | $4 \times 10^5$ oocysts |
| E. maxima | CP | $4 \times 10^5$ oocysts |
| E. mitis | HP | $4 \times 10^6$ oocysts |
| E. necatrix | HP | $2 \times 10^6$ oocysts |
| E. praecox | HP | $4 \times 10^5$ oocysts |
| E. tenella | HP | $2 \times 10^6$ oocysts |
| xanthan gum | | 6 g |
| water | | to 1 liter |

The addition of 25 ml of this vaccine to 500 ml of drinking water provides sufficient vaccine in xanthan gum at a final concentration of 0.03% w/v for 100 chickens.

EXAMPLE 3

500 ml of vaccine containing 5000 doses may be formulated as follows:

| | | |
|---|---|---|
| E. acervulina | HP71s + 9 | $2.5 \times 10^6$ oocysts |
| E. brunetti | HP27s + 4 | $5 \times 10^5$ oocysts |
| E. maxima | MFP15s + 5 | $5 \times 10^5$ oocysts |
| E. maxima | CP12s + 5 | $5 \times 10^5$ oocysts |
| E. mitis | HP12s + 7 | $5 \times 10^6$ oocysts |
| E. necatrix | HP42s + 5 | $2.5 \times 10^6$ oocysts |
| E. praecox | HP21s + 3 | $5 \times 10^5$ oocysts |
| E. tenella | HP38s + 2 | $2.5 \times 10^6$ oocysts |
| xanthan gum | | 7.5 g |
| water | | to 500 ml |

The addition of 10 ml of this vaccine to 500 ml of drinking water provides sufficient vaccine in xanthan gum at a final concentration of 0.03% w/v for 100 chickens.

EXAMPLE 4

(a) 500 ml of vaccine containing 5000 doses may be formulated as follows:

| | | |
|---|---|---|
| E. acervulina | HP71s + 9 | $2.5 \times 10^6$ oocysts |
| E. brunetti | HP27s + 4 | $5 \times 10^5$ oocysts |
| E. maxima | MFP15s + 5 | $5 \times 10^5$ oocysts |
| E. maxima | CP12s + 5 | $5 \times 10^5$ oocysts |
| E. mitis | HP12s + 7 | $5 \times 10^6$ oocysts |
| E. necatrix | HP42s + 5 | $2.5 \times 10^6$ oocysts |
| E. praecox | HP21s + 3 | $5 \times 10^5$ oocysts |
| E. tenella | HP38s + 2 | $2.5 \times 10^6$ oocysts |
| xanthan gum | | 3.0 g |
| water | | to 500 ml |

The addition of 10 ml of this vaccine to 500 ml of drinking water provides sufficient vaccine in xanthan gum at a final concentration of 0.012% w/v for 100 chickens.

(b) 500 ml of vaccine containing 5000 doses may be formulated as follows:

| | | | |
|---|---|---|---|
| E. acervulina | HP71s + 13 | ECACC 86072203 | $2.5 \times 10^6$ oocysts |
| E. brunetti | HP27s + 8 | ECACC 86112013 | $5 \times 10^5$ oocysts |
| E. maxima | MFP15s + 11 | ECACC 86112011 | $5 \times 10^5$ oocysts |
| E. maxima | CP12s + 11 | ECACC 86112012 | $5 \times 10^5$ oocysts |
| E. mitis | HP12s + 11 | ECACC 86072206 | $5 \times 10^6$ oocysts |
| E. necatrix | HP42.2s + 8 | ECACC 86072202 | $2.5 \times 10^6$ oocysts |
| E. praecox | HP21.2s + 2 | ECACC 86072205 | $5 \times 10^5$ oocysts |
| E. tenella | HP38s + 10 | ECACC 86072201 | $2.5 \times 10^6$ oocysts |
| xanthan gum | | | 3.0 g |
| water | | | to 500 ml |

The addition of 10 ml of this vaccine to 500 ml of drinking water provides sufficient vaccine in xanthan gum at a final concentration of 0.012% w/v for 100 chickens.

EXAMPLE 5

Parent strains of the seven Eimeria species were subjected to serial passage with selection for shortened prepatent times as described above. The reproduction of the various attenuated lines was determined by oral inoculation of batches of Light Sussex chickens and counting the average number of oocysts produced by each bird. The immunogenicity of the attenuated lines was also determined by experiments in which chickens given a primary inoculation of oocysts were challenged with oocysts of the parent strain. The average outputs of oocysts per bird were determined and the percentage protection calculated from reference to the output of oocysts by challenged controls. The pathogenicity of the attenuated lines as compared with the parent strain was also determined by inoculation of batches of weight-matched Light Sussex chickens with a standard dose of each parasite and determining body weight after twelve to fourteen days as compared with uninfected controls and those given the non-attenuated parent strain.

The results are shown in the following Tables 1 and 2.

TABLE 1

| Species | Reference of precocious line (code) | No. oocysts dosed (thousands) | Start weight (g) of birds | No. days of test | Final weight of birds (g) | | |
|---|---|---|---|---|---|---|---|
| | | | | | Uninfected Control | Precocious Line (Weight reduction cf. control) | Parent Strain (Weight reduction cf. control) |
| E. acervulina HP | 71s + 21 | 100 | 305 | 10 | 522 | 519 (3) | 476 (46) |
| E. brunetti HP | 27s + 9 | 50 | 158 | 14 | 401 | 370 (31) | 310 (91) |
| E. maxima MFP | 15s + 10 | 50 | 157 | 14 | 408 | 391 (17) | 343 (65) |
| E. maxima CP | 12s + 15 | 50 | 165 | 14 | 445 | 416 (29) | 354 (91) |
| E. mitis HP | 12s + 17 | 100 | 210 | 12 | 408 | 415 (7)* | 375 (33) |
| E. necatrix HP | 42s + 11 | 50 | 168 | 14 | 426 | 384 (42) | 304 (122) |
| E. praecox HP | 21s + 9 | 1000 | 250 | 12 | 512 | 506 (6) | 490 (22) |
| E. tenella HP | 38s + 19 | 50 | 289 | 10 | 482 | 479 (3) | 431 (49) |

*Increase in Weight

TABLE 2

| Species and Precocious Line | Passage | Dose (oocysts/ bird × $10^2$) | Challenge (oocysts/ bird × $10^2$) | Output post (oocysts/ bird × $10^6$) | Percentage Protection |
|---|---|---|---|---|---|
| E. acervulina HP | 42 | 1000 | 100 | 2.5 | 98.6 |
| none | — | nil | 100 | 172.6 | — |
| E. brunetti HP | 26 | 0.5 | 1 | <0.01 | >99.9 |
| none | — | nil | 1 | 30.30 | — |
| E. maxima MFP | 15 | 2.5 | 5 | <0.01 | >99.9 |
| none | — | nil | 5 | 59.90 | — |
| E. maxima CP | 10 | 2.5 | 5 | <0.01 | >99.9 |
| none | — | nil | 5 | 61.40 | — |
| E. mitis HP | 12s + 3 | 1000 | 100 | 20.0 | 84.2 |
| HMF | — | nil | 100 | 126.4 | — |
| E. necatrix HP | 38 | 10 | 5 | 0.47 | 95.8 |
| none | — | nil | 5 | 11.27 | — |
| E. praecox HP | 19 | 10 | 10 | <0.01 | >99.9 |
| none | — | nil | 10 | 230.5 | — |
| E. tenella HP | 38s + 6 | 5 | 10 | 36.0 | 73.3 |
| none | — | nil | 10 | 135.0 | — |

EXAMPLE 6

Vaccine Trial

The vaccine of Example 3 was used in a trial conducted on 4,480 Cobb broiler chickens kept in floor pens. The concentration of xanthan gum in the vaccine was adjusted so that administration of 140 doses of vaccine to each drinking vessel provided a final xanthan gum concentration of 0.03%. The trial was designed to compare the performance of birds vaccinated with live attenuated coccidiosis vaccine of the invention and birds fed the coccidiostat, monensin, in the face of a challenge with seven homologous or seven heterologous strains of each of the seven species of Eimeria. The heterologous strains were chosen on the basis that they were either thought to be more pathogenic than the homologous ones or antigenically distinct.

Birds were penned in groups of 140. Four pens were allocated to each treatment and two pens were allocated to each control group. Hence each treatment involved 560 birds and each control involved 280 birds. The allocation of pens to treatment was randomised throughout the broiler house. The design of the trial was as follows:

TABLE 3

| Treatment | Homologous Challenge Day 31 | Heterologous Challenge Day 31 |
|---|---|---|
| Vaccine (day 7) | Group 1 | Group 2 |
| Monensin (day 1–45) 100 ppm | Group 3 | Group 4 |
| Robenidine (day 1–28) 33 ppm | Group 5 | Group 6 |

Groups 1–4 = 560 birds
Groups 5–6 = 280 birds

The vaccine was administered via the drinking water. The birds were fed a ration based on a commercial formulation which included the antibiotic growth promoter avoparcin at 10 ppm. The anticoccidial drugs were administered in the feed.

It should be noted that, in order to prevent infection by wild Eimeria strains, and consequent development of immunity, the two control groups were fed robenidine (30 ppm) for 28 days. One group received a heterologous challenge and the other received a homologous challenge.

All birds received an individual oral challenge administered by inoculation into the crop on day 31. The numbers of oocysts of each species in the challenge doses were as follows:

TABLE 4

| Species | Homologous | Heterologous | Oocysts/bird (× $10^3$) |
|---|---|---|---|
| E. acervulina | H | | 200 |
| | | HG | 200 |

TABLE 4-continued

| Species | Homologous | Heterologous | Oocysts/bird ($\times 10^3$) |
|---|---|---|---|
| E. brunetti | H | | 10 |
| | | FS339 | 10 |
| E. maxima | MF | | 5 |
| | | London Road | 10 |
| E. mitis | H | | 72 |
| | | Watchill | 88 |
| E. necatrix | H | | 40 |
| | | Buxted | 25 |
| E. praecox | H | | 200 |
| | | SM8 | 200 |
| E. tenella | H | | 30 |
| | | FD | 30 |

Liveweights and cumulative feed intakes were measured on days 30, 37 and 49. Feed conversion ratios were calculated by dividing the feed intake by the gain in liveweight from day 1. Counts of oocysts in the litter were made for each pen at weekly intervals. On day 37, a sample of 5 birds from each pen (total 160) was culled and coccidiosis lesion scores were estimated. Scores were made on a scale of 0 to 3.5 in ascending severity of the lesions symptomatic of infection with E. acervulina, E. brunetti, E. maxima/necatrix (grouped together because they are difficult to distinguish) and E. tenella. Mean lesion scores were calculated.

RESULTS

Liveweights

At the end of the trial (day 49) the vaccinated groups were all marginally heavier than the monensin treated groups but the differences were not significant. The liveweights of the respective group of birds are shown in Table 5 hereinafter.

Feed Intake and Feed Conversion Ratios

At the end of the trial differences in the feed intake and feed conversion ratios between the vaccinated and monensin treated groups were not statistically significant.

Lesion Scores

Both vaccination and monensin treatment resulted in lower lesion scores after either homologous or heterologous challenge. However, the protection afforded by the vaccine against heterologous challenge was superior to that afforded by monensin with respect to E. acervulina, E. brunetti and particularly E. tenella. Slightly elevated scores for heterologous E. maxima/necatrix were observed in both vaccinated and monensin treated birds, but in each case these were lower than the controls. Lesion scores in respect of the respective groups of birds are shown in Table 6 hereinafter.

Counts of oocysts in the litter

There was a very high pen to pen variation with these counts. However, after challenge with heterologous strains, the counts in the pens of monensin treated birds were, on average two or three times higher than those in the pens of vaccinated birds.

Conclusion

The performance of the birds showed that overall the vaccine of the invention and monensin were equally effective in protecting against coccidial challenge. The vaccine withstood the heterologous challenge well and exhibited a particularly prominent advantage over monensin with respect to the heterologous E. tenella challenge.

TABLE 5

| | | LIVEWEIGHTS (g/bird) | |
|---|---|---|---|
| Day | Treatment | Homologous Challenge | Heterologous Challenge |
| 49 | Vaccine | 2492 | 2429 |
| | Monensin | 2489 | 2407 |
| | Control* | 2225 | 2197 |

*Robenidine withdrawn at day 28

TABLE 6

| | | | LESION SCORES | | | |
|---|---|---|---|---|---|---|
| | | | | Mean Lesion Score | | |
| Challenge | Treatment | Sample Size | E. acervulina | E. brunetti | E. maxima/ necatrix | E. tenella |
| Homologous | Vaccine | 20 | 0 | 0 | 0.13 | 0 |
| | Monensin | 20 | 0 | 0.03 | 0.13 | 0.20 |
| | Control | 10 | 0.2 | 0.40 | 1.25 | 2.25 |
| Heterologous | Vaccine | 20 | 0 | 0 | 0.40 | 0.10 |
| | Monensin | 20 | 0.10 | 0 | 0.95 | 1.53 |
| | Control | 10 | 0.30 | 0.70 | 2.00 | 2.65 |

We claim:

1. A live vaccine for use in combating coccidiosis in chickens comprising an effective concentration of live sporulated oocysts of a strain of Eimeria acervulina having a prepatent time in chickens between 60 and 84 hours, of a strain of Eimeria maxima having a prepatent time in chickens of between 80 and 120 hours, of a strain of Eimeria tenella having a prepatent time in chickens between 90 and 125 hours, of a strain of Eimeria necatrix having a prepatent time in chickens between 90 and 126 hours, of a strain of Eimeria mitis having a prepatent time in chickens between 60 and 84 hours, of a strain of Eimeria brunetti having a prepatent time in chickens between 70 and 110 hours, and of live sporulated oocysts of a strain of Eimeria praecox having a prepatent time in chickens between 44 and 75 hours and an effective carrier.

2. The vaccine of claim 1 wherein the number of said sporulated oocysts of Eimeria maxima is 15-30 per 100 sporulated oocysts of Eimeria acervulina and the number of sporulated oocysts of Eimeria tenella is 70-110 per 100 sporulated oocysts of Eimeria acervulina.

3. The vaccine of claim 2 wherein the number of said sporulated oocysts of Eimeria brunetti is 15-30 per 100 sporulated oocysts of Eimeria acervulina; the number of said sporulated oocysts of said Eimeria mitis is 180-220 per 100 sporulated oocysts of Eimeria acervulina; and the number of said sporulated oocysts of said Eimeria necatrix is 70-100 per 100 sporulated oocysts of Eimeria acervulina.

4. The vaccine of claim 3 wherein the number of sporulated oocysts of said *Eimeria praecox* is 15-25 per 100 sporulated oocysts of *Eimeria acervulina*.

5. The vaccine of claim 1 wherein the number of said sporulated oocysts of *Eimeria maxima* is 18-22 per 100 sporulated oocysts of *Eimeria acervulina* and the number of said sporulated oocysts of *Eimeria tenella* is 75-105 per 100 sporulated oocysts of *Eimeria acervulina*.

6. The vaccine of claim 5 wherein the number of said sporulated oocysts of *Eimeria brunetti* is 18-22 per 100 sporulated oocysts of *Eimeria acervulina*; and the number of said sporulated oocysts of *Eimeria mitis* is 190-210 per 100 sporulated oocysts of *Eimeria acervulina*; and the number of sporulated oocysts of said *Eimeria necatrix* is 75-105 per 100 sporulated oocysts of *Eimeria acervulina*.

7. The vaccine of claim 6 wherein the number of said sporulated oocysts of *Eimeria praecox* is 18-22 per 100 sporulated oocysts of *Eimeria acervulina*.

8. A vaccine as claimed in claim 1 in dosage unit form in which each dosage unit contains 50 to 25,000 of said oocysts of *Eimeria acervuling*, 10 to 5,000 of said oocysts of *Eimeria maxima* and 50 to 25,000 of said oocysts of *Eimeria tenella*.

9. A vaccine as claimed in claim 1 in dosage unit form in which each dosage unit contains 50 to 25,000 of said oocysts of *Eimeria acervulina*, 10 to 5,000 of said oocysts of *Eimeria maxima*, 50 to 25,000 of said oocysts of *Eimeria tenella*, 10 to 5,000 of said oocysts of *Eimeria brunetti*, 100 to 50,000 of said oocysts of *Eimeria mitis*, 50 to 25,000 of said oocysts of *Eimeria necatrix*.

10. A vaccine as claimed in claim 1 in dosage unit form in which each dosage unit contains 50 to 25,000 of said oocysts of *Eimeria acervulina*, 10 to 5,000 of said oocysts of *Eimeria maxima*, 50 to 25,000 of said oocysts of *Eimeria tenella*, 10 to 5,000 of said oocysts of *Eimeria brunetti*, 100 to 50,000 of said oocysts of *Eimeria mitis*, 50 to 25,000 of said oocysts of *Eimeria necatrix*, and 10 to 5,000 of said oocysts of *Eimeria praecox*.

11. A vaccine as claimed in claim 1 in which the said Eimeria strains are stable after 5 neutral or relaxed passages in chickens.

12. A vaccine as claimed in claim 1 in which the said strain of *Eimeria acervulina* is *E. acervulina* ECACC 86072203, the said strain of *Eimeria tenella* is *E. Tennella* ECACC 86072201 and the said strain of *Eimeria maxima* is *E. maxima* ECACC 86112011 and/or ECACC 86112012.

13. A vaccine as claimed in claim 1 in which the said strain of *Eimeria mitis* is *E. mitis* ECACC 86072206, the said strain of *Eimeria mitis* is *E. mitis* ECACC 86072206, the said strain of *Eimeria necatrix* is *E. necatrix* ECACC 86072202 and the said strain of *Eimeria brunetti* is *E. brunetti* ECACC 86112013.

14. A vaccine as claimed in claim 1 in which the said strain of *Eimeria mitis* is *E. mitis* ECACC 86072206, the said strain of *Eimeria necatrix* is *E. necatrix* ECACC 86072202 and the said strain of *Eimeria brunetti* is *E. brunetti* ECACC 86072204.

15. A vaccine as claimed in claim 1 in which the said strain of *Eimeria praecox* is *E. praecox* ECACC 86072205.

16. A process for the preparation of a vaccine as claimed in claim 1 which comprises sporulating oocysts of the said Eimeria strains and admixing them with a carrier and/or adjuvant.

17. A method of inhibiting coccidiosis in chickens which comprises administering to the chickens an effective amount of a vaccine as claimed in claim 1.

18. A method as claimed in claim 17 in which the vaccine is administered in the drinking water of the chickens.

* * * * *